(12) United States Patent
Kugler et al.

(10) Patent No.: US 11,826,070 B2
(45) Date of Patent: *Nov. 28, 2023

(54) ENDOVASCULAR DEVICES AND METHODS

(71) Applicant: BOSTON SCIENTIFIC SCIMED, INC., Maple Grove, MN (US)

(72) Inventors: Chad J. Kugler, Buffalo, MN (US); Robert E. Atkinson, Lake Elmo, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 326 days.

This patent is subject to a terminal disclaimer.

(21) Appl. No.: 17/306,420

(22) Filed: May 3, 2021

(65) Prior Publication Data

US 2021/0251648 A1    Aug. 19, 2021

Related U.S. Application Data

(63) Continuation of application No. 16/419,574, filed on May 22, 2019, now Pat. No. 11,020,141, which is a
(Continued)

(51) Int. Cl.
*A61B 17/3203* (2006.01)
*A61B 17/221* (2006.01)
(Continued)

(52) U.S. Cl.
CPC ........ *A61B 17/32037* (2013.01); *A61B 17/22* (2013.01); *A61B 17/221* (2013.01);
(Continued)

(58) Field of Classification Search
CPC .......... A61B 17/3403; A61B 17/3415; A61M 25/04; A61M 25/007; A61M 29/02
See application file for complete search history.

(56) References Cited

U.S. PATENT DOCUMENTS 4,020,829 A    5/1977  Wilson et al.
4,233,983 A    11/1980 Rocco
(Continued)

FOREIGN PATENT DOCUMENTS

WO      0178822 A2    10/2001
WO   2007033052 A2    3/2007
(Continued)

OTHER PUBLICATIONS

Columbo, Antonio, et al; "Treating Chronic Total Occlusions Using Subliminal Tracking and Reentry: The Star Technique," Catheterization and Cardiovascular Interventions, vol. 64:407-411 (2005).
(Continued)

*Primary Examiner* — Bradley J Osinski
(74) *Attorney, Agent, or Firm* — Seager, Tufte & Wickhem LLP

(57) ABSTRACT

Devices and methods for the treatment of chronic total occlusions are provided. One disclosed embodiment comprises a method of facilitating treatment via a vascular wall defining a vascular lumen containing an occlusion therein. The method includes providing an intravascular device having a distal portion with a side port, inserting the device into the vascular lumen, positioning the distal portion in the vascular wall, directing the distal portion within the vascular wall such that the distal portion moves at least partially laterally, and directing the side port towards the vascular lumen.

20 Claims, 17 Drawing Sheets

Related U.S. Application Data continuation of application No. 13/079,179, filed on Apr. 4, 2011, now Pat. No. 10,342,569, which is a continuation of application No. 11/518,428, filed on Sep. 11, 2006, now Pat. No. 7,938,819.

(60) Provisional application No. 60/727,819, filed on Oct. 18, 2005, provisional application No. 60/717,726, filed on Sep. 15, 2005, provisional application No. 60/716,287, filed on Sep. 12, 2005.

(51) Int. Cl.
*A61F 2/88* (2006.01)
*A61B 17/22* (2006.01)
*A61M 29/02* (2006.01)
*A61B 17/32* (2006.01)
*A61B 17/3207* (2006.01)
*A61B 17/00* (2006.01)
*A61M 25/00* (2006.01)
*A61M 25/01* (2006.01)

(52) U.S. Cl.
CPC .......... *A61B 17/22031* (2013.01); *A61F 2/88* (2013.01); *A61M 29/02* (2013.01); *A61B 17/00008* (2013.01); *A61B 2017/00252* (2013.01); *A61B 2017/22034* (2013.01); *A61B 2017/22077* (2013.01); *A61B 2017/22094* (2013.01); *A61B 2017/22095* (2013.01); *A61B 2017/320056* (2013.01); *A61B 2017/320064* (2013.01); *A61B 2017/320733* (2013.01); *A61B 2017/320741* (2013.01); *A61M 25/0026* (2013.01); *A61M 2025/006* (2013.01); *A61M 2025/0197* (2013.01)

(56) References Cited

U.S. PATENT DOCUMENTS

| | | |
|---|---|---|
| 4,569,347 A | 2/1986 | Frisbie |
| 4,581,017 A | 4/1986 | Sabota |
| 4,621,636 A | 11/1986 | Fogarty |
| 4,747,821 A | 5/1988 | Kensey et al. |
| 4,762,130 A | 8/1988 | Fogarty et al. |
| 4,774,949 A | 10/1988 | Fogarty |
| 4,819,634 A | 4/1989 | Shiber |
| 4,878,495 A | 11/1989 | Grayzel |
| 4,976,689 A | 12/1990 | Buchbinder et al. |
| 4,979,939 A | 12/1990 | Shiber |
| 4,990,134 A | 2/1991 | Auth |
| 5,071,406 A | 12/1991 | Jang |
| 5,127,917 A | 7/1992 | Nederhauser et al. |
| 5,193,546 A | 3/1993 | Shaknovich |
| 5,201,753 A | 4/1993 | Lampropoulos et al. |
| 5,263,493 A | 11/1993 | Avitall |
| 5,275,610 A | 1/1994 | Eberbach |
| 5,324,263 A | 6/1994 | Kraus et al. |
| 5,356,418 A | 10/1994 | Shturman |
| 5,372,587 A | 12/1994 | Hammerslag et al. |
| 5,383,856 A | 1/1995 | Bersin |
| 5,385,152 A | 1/1995 | Abele et al. |
| 5,409,453 A | 4/1995 | Lundquist et al. |
| 5,415,637 A | 5/1995 | Khosravi |
| 5,464,395 A | 11/1995 | Faxon et al. |
| 5,501,667 A | 3/1996 | Verdun, Jr. |
| 5,505,702 A | 4/1996 | Arney |
| 5,534,007 A | 7/1996 | St. Germain et al. |
| 5,555,883 A | 9/1996 | Avitall |
| 5,571,122 A | 11/1996 | Kelly et al. |
| 5,571,169 A | 11/1996 | Plaia et al. |
| 5,603,720 A | 2/1997 | Kieturakis |
| 5,643,298 A | 7/1997 | Nordgren et al. |
| 5,645,529 A | 7/1997 | Fagan et al. |
| 5,655,548 A | 8/1997 | Nelson et al. |
| 5,695,506 A | 12/1997 | Pike et al. |
| 5,728,133 A | 3/1998 | Kontos |
| 5,741,270 A | 4/1998 | Hansen et al. |
| 5,741,429 A | 4/1998 | Donadio, III et al. |
| 5,779,721 A | 7/1998 | Nash |
| 5,783,227 A | 7/1998 | Dunham |
| 5,807,241 A | 9/1998 | Heimberger |
| 5,824,071 A | 10/1998 | Nelson et al. |
| 5,830,222 A | 11/1998 | Makower |
| 5,830,224 A | 11/1998 | Cohn et al. |
| 5,843,050 A | 12/1998 | Jones et al. |
| 5,910,133 A | 6/1999 | Gould |
| 5,916,194 A | 6/1999 | Jacobsen et al. |
| 5,935,108 A | 8/1999 | Katoh et al. |
| 5,944,686 A | 8/1999 | Patterson et al. |
| 5,954,713 A | 9/1999 | Newman et al. |
| 5,957,900 A | 9/1999 | Ouchi |
| 5,968,064 A | 10/1999 | Selmon et al. |
| 5,989,276 A | 11/1999 | Houser et al. |
| 6,010,449 A | 1/2000 | Selmon et al. |
| 6,013,055 A | 1/2000 | Bampos et al. |
| 6,015,405 A | 1/2000 | Schwartz et al. |
| 6,022,343 A | 2/2000 | Johnson et al. |
| 6,036,707 A | 3/2000 | Spaulding |
| 6,059,750 A | 5/2000 | Fogarty et al. |
| 6,068,638 A | 5/2000 | Makower |
| 6,071,281 A | 6/2000 | Burnside et al. |
| 6,071,292 A | 6/2000 | Makower et al. |
| 6,081,738 A | 6/2000 | Hinohara et al. |
| 6,099,542 A | 8/2000 | Cohn et al. |
| 6,117,064 A | 9/2000 | Apple et al. |
| 6,120,516 A | 9/2000 | Selmon et al. |
| 6,126,649 A | 10/2000 | VanTassel et al. |
| 6,155,264 A | 12/2000 | Ressemann et al. |
| 6,157,852 A | 12/2000 | Selmon et al. |
| 6,159,225 A | 12/2000 | Makower |
| 6,183,432 B1 | 2/2001 | Milo |
| 6,186,972 B1 | 2/2001 | Nelson et al. |
| 6,190,353 B1 | 2/2001 | Makower et al. |
| 6,203,559 B1 | 3/2001 | Davis et al. |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,235,000 B1 | 5/2001 | Milo et al. |
| 6,241,667 B1 | 6/2001 | Vetter et al. |
| 6,246,914 B1 | 6/2001 | de la Rama et al. |
| 6,254,588 B1 | 7/2001 | Jones et al. |
| 6,258,052 B1 | 7/2001 | Milo |
| 6,266,550 B1 | 7/2001 | Selmon et al. |
| 6,277,133 B1 | 8/2001 | Kanesaka |
| 6,283,940 B1 | 9/2001 | Mulholland |
| 6,283,951 B1 | 9/2001 | Flaherty et al. |
| 6,283,983 B1 | 9/2001 | Makower et al. |
| 6,287,317 B1 | 9/2001 | Makower et al. |
| 6,302,875 B1 | 10/2001 | Makower et al. |
| 6,330,884 B1 | 12/2001 | Kim |
| 6,337,142 B2 | 1/2002 | Harder et al. |
| 6,358,244 B1 | 3/2002 | Newman et al. |
| 6,375,615 B1 | 4/2002 | Flaherty et al. |
| 6,379,319 B1 | 4/2002 | Garibotto et al. |
| 6,387,119 B2 | 5/2002 | Wolf et al. |
| 6,398,798 B2 | 6/2002 | Selmon et al. |
| 6,416,523 B1 | 7/2002 | Lafontaine |
| 6,428,552 B1 | 8/2002 | Sparks |
| 6,432,127 B1 | 8/2002 | Kim et al. |
| 6,447,539 B1 | 9/2002 | Nelson et al. |
| 6,475,226 B1 | 11/2002 | Belef et al. |
| 6,485,458 B1 | 11/2002 | Takahashi |
| 6,491,660 B2 | 12/2002 | Guo et al. |
| 6,491,707 B2 | 12/2002 | Makower et al. |
| 6,506,178 B1 | 1/2003 | Schubart et al. |
| 6,508,824 B1 | 1/2003 | Flaherty et al. |
| 6,508,825 B1 | 1/2003 | Selmon et al. |
| 6,511,458 B2 | 1/2003 | Milo et al. |
| 6,514,217 B1 | 2/2003 | Selmon et al. |
| 6,544,230 B1 | 4/2003 | Flaherty et al. |
| 6,561,998 B1 | 5/2003 | Roth et al. |

(56) References Cited

U.S. PATENT DOCUMENTS

| | | |
|---|---|---|
| 6,565,583 B1 | 5/2003 | Deaton et al. |
| 6,569,143 B2 | 5/2003 | Alchas et al. |
| 6,569,145 B1 | 5/2003 | Shmulewitz et al. |
| 6,569,150 B2 | 5/2003 | Teague et al. |
| 6,579,311 B1 | 6/2003 | Makower |
| 6,589,164 B1 | 7/2003 | Flaherty |
| 6,599,304 B1 | 7/2003 | Selmon et al. |
| 6,602,241 B2 | 8/2003 | Makower et al. |
| 6,613,081 B2 | 9/2003 | Kim et al. |
| 6,616,675 B1 | 9/2003 | Evard et al. |
| 6,623,448 B2 | 9/2003 | Slater |
| 6,638,247 B1 | 10/2003 | Selmon et al. |
| 6,638,293 B1 | 10/2003 | Makower et al. |
| 6,655,386 B1 | 12/2003 | Makower et al. |
| 6,656,195 B2 | 12/2003 | Peters et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,685,716 B1 | 2/2004 | Flaherty et al. |
| 6,694,983 B2 | 2/2004 | Wolf et al. |
| 6,709,444 B1 | 3/2004 | Makower |
| 6,719,725 B2 | 4/2004 | Milo et al. |
| 6,726,677 B1 | 4/2004 | Flaherty et al. |
| 6,746,426 B1 | 6/2004 | Flaherty et al. |
| 6,746,462 B1 | 6/2004 | Selmon et al. |
| 6,746,464 B1 | 6/2004 | Makower |
| 6,786,884 B1 | 9/2004 | DeCant, Jr. et al. |
| 6,800,085 B2 | 10/2004 | Selmon et al. |
| 6,824,550 B1 | 11/2004 | Noriega et al. |
| 6,830,577 B2 | 12/2004 | Nash et al. |
| 6,837,868 B1 | 1/2005 | Fajnsztajn |
| 6,860,892 B1 | 3/2005 | Tanaka et al. |
| 6,863,684 B2 | 3/2005 | Kim et al. |
| 6,866,676 B2 | 3/2005 | Kieturakis et al. |
| 6,884,225 B2 | 4/2005 | Kato et al. |
| 6,905,505 B2 | 6/2005 | Nash et al. |
| 6,929,009 B2 | 8/2005 | Makower et al. |
| 6,936,056 B2 | 8/2005 | Nash et al. |
| 6,942,641 B2 | 9/2005 | Seddon |
| 6,949,125 B2 | 9/2005 | Robertson |
| 6,991,617 B2 | 1/2006 | Hektner et al. |
| 7,004,173 B2 | 2/2006 | Sparks et al. |
| 7,056,325 B1 | 6/2006 | Makower et al. |
| 7,059,330 B1 | 6/2006 | Makower et al. |
| 7,083,588 B1 | 8/2006 | Shmulewitz et al. |
| 7,094,230 B2 | 8/2006 | Flaherty et al. |
| 7,105,031 B2 | 9/2006 | Letort |
| 7,134,438 B2 | 11/2006 | Makower et al. |
| 7,137,990 B2 | 11/2006 | Hebert et al. |
| 7,159,592 B1 | 1/2007 | Makower et al. |
| 7,179,270 B2 | 2/2007 | Makower |
| 7,191,015 B2 | 3/2007 | Lamson et al. |
| 7,229,421 B2 | 6/2007 | Jen et al. |
| 7,316,655 B2 | 1/2008 | Garibotto et al. |
| 7,377,910 B2 | 5/2008 | Katoh et al. |
| 7,465,286 B2 | 12/2008 | Patterson et al. |
| 2001/0000041 A1 | 3/2001 | Selmon et al. |
| 2001/0056273 A1 | 12/2001 | C. |
| 2002/0029052 A1 | 3/2002 | Evans et al. |
| 2002/0052637 A1 | 5/2002 | Houser et al. |
| 2002/0103459 A1 | 8/2002 | Sparks et al. |
| 2003/0028200 A1 | 2/2003 | Berg et al. |
| 2003/0040737 A1 | 2/2003 | Merril et al. |
| 2003/0109809 A1 | 6/2003 | Jen et al. |
| 2003/0120195 A1 | 6/2003 | Milo et al. |
| 2003/0236542 A1 | 12/2003 | Makower |
| 2004/0015193 A1 | 1/2004 | Lamson et al. |
| 2004/0059280 A1 | 3/2004 | Makower et al. |
| 2004/0102719 A1 | 5/2004 | Keith et al. |
| 2004/0133225 A1 | 7/2004 | Makower |
| 2004/0158143 A1 | 8/2004 | Flaherty et al. |
| 2004/0167554 A1 | 8/2004 | Simpson et al. |
| 2004/0230156 A1 | 11/2004 | Schreck et al. |
| 2004/0249277 A1 | 12/2004 | Kato et al. |
| 2004/0249338 A1 | 12/2004 | DeCant, Jr. et al. |
| 2005/0038467 A1 | 2/2005 | Hebert et al. |
| 2005/0049574 A1 | 3/2005 | Petrick et al. |
| 2005/0171478 A1 | 8/2005 | Selmon et al. |
| 2005/0177105 A1 | 8/2005 | Shalev |
| 2005/0216044 A1 | 9/2005 | Hong |
| 2005/0261663 A1 | 11/2005 | Patterson et al. |
| 2006/0094930 A1 | 5/2006 | Sparks et al. |
| 2006/0135984 A1 | 6/2006 | Kramer et al. |
| 2006/0229646 A1 | 10/2006 | Sparks |
| 2006/0271078 A1 | 11/2006 | Modesitt |
| 2007/0083220 A1 | 4/2007 | Shamay |
| 2007/0088230 A1 | 4/2007 | Terashi et al. |
| 2007/0093779 A1 | 4/2007 | Kugler et al. |
| 2007/0093780 A1 | 4/2007 | Kugler et al. |
| 2007/0093781 A1 | 4/2007 | Kugler et al. |
| 2007/0093782 A1 | 4/2007 | Kugler et al. |
| 2007/0093783 A1 | 4/2007 | Kugler et al. |
| 2007/0265596 A1 | 11/2007 | Jen et al. |
| 2008/0103443 A1 | 5/2008 | Kabrick et al. |
| 2008/0228171 A1 | 9/2008 | Kugler et al. |
| 2008/0243065 A1 | 10/2008 | Rottenberg et al. |
| 2008/0243067 A1 | 10/2008 | Rottenberg et al. |
| 2009/0088685 A1 | 4/2009 | Kugler et al. |
| 2009/0124899 A1 | 5/2009 | Jacobs et al. |
| 2009/0209910 A1 | 8/2009 | Kugler et al. |
| 2009/0270890 A1 | 10/2009 | Robinson et al. |
| 2010/0063534 A1 | 3/2010 | Kugler et al. |
| 2010/0069945 A1 | 3/2010 | Olson et al. |

FOREIGN PATENT DOCUMENTS

| | | |
|---|---|---|
| WO | 2008063621 A2 | 5/2008 |
| WO | 2009054943 A1 | 4/2009 |
| WO | 2009100129 A2 | 8/2009 |
| WO | 2009134346 A2 | 11/2009 |
| WO | 2010019241 A1 | 2/2010 |
| WO | 2010044816 A1 | 4/2010 |

OTHER PUBLICATIONS

International Search Report in PCT/US06/35244 dated Mar. 24, 2008.
Written Opinion of International Searching Authority in PCT/US06/35244 dated Mar. 24, 2008.
International Preliminary Report on Patentability in PCT/US06/35244 dated Mar. 26, 2009.
Office Action for U.S. Appl. No. 11/518,521 dated May 24, 2010 (9 pages).
Office Action for U.S. Appl. No. 11/518,521 dated Dec. 23, 2009 (10 pages).
Office Action for U.S. Appl. No. 11/518,521 dated Mar. 20, 2009 (9 pages).

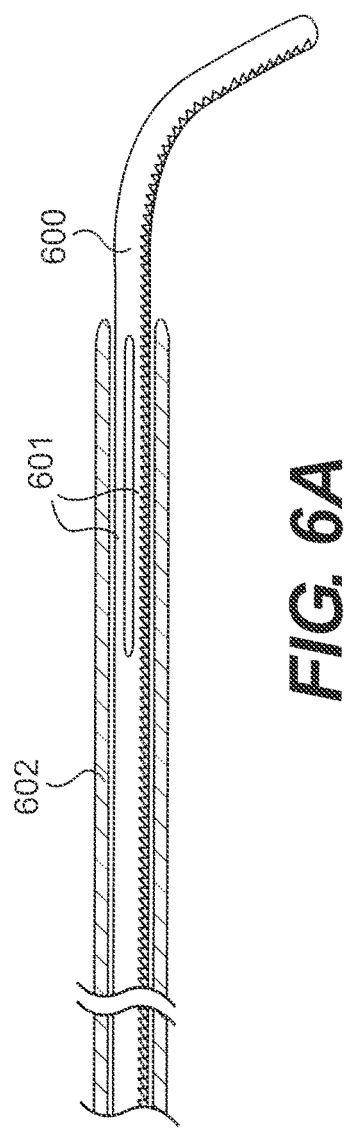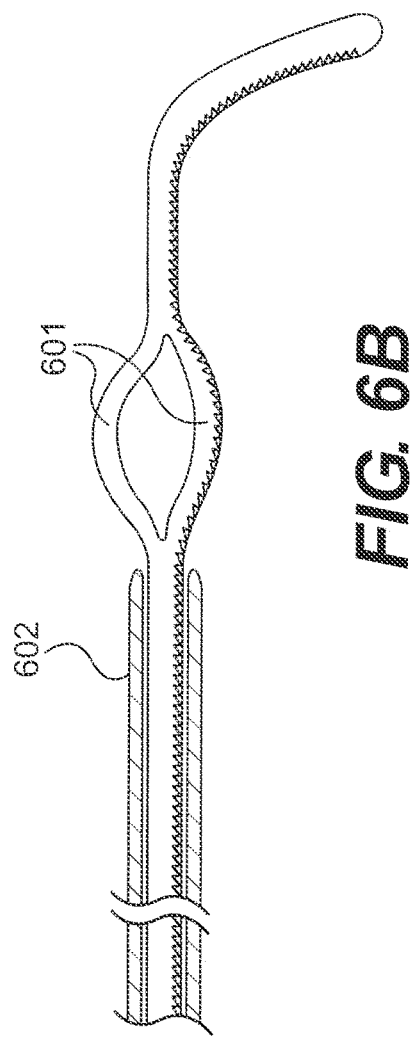

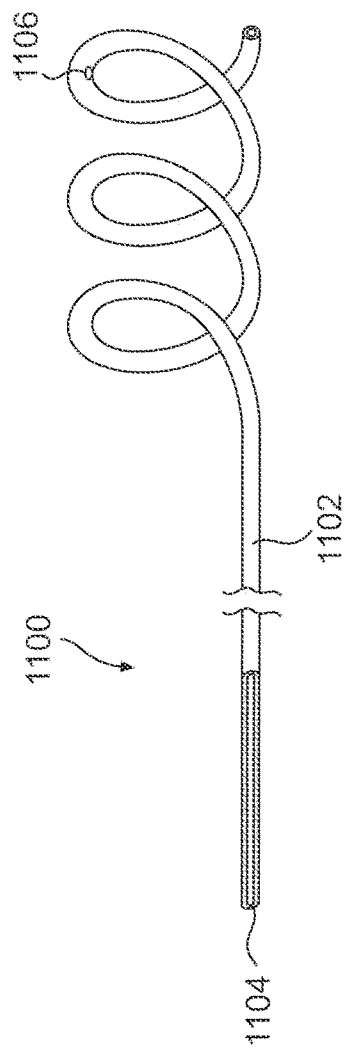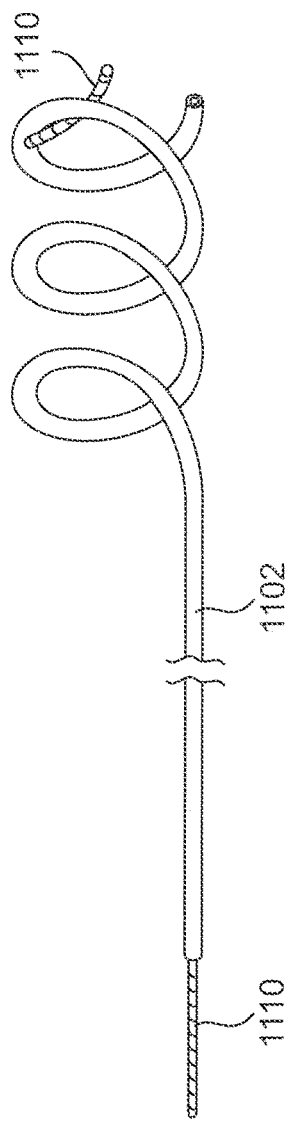

ENDOVASCULAR DEVICES AND METHODS

CROSS REFERENCE TO RELATED APPLICATIONS

This is a continuation of U.S. application Ser. No. 16/419,574, filed May 22, 2019, which is a continuation of U.S. application Ser. No. 13/079,179, filed Apr. 4, 2011, now U.S. Pat. No. 10,342,569, which is a continuation of U.S. application Ser. No. 11/518,428, filed Sep. 11, 2006, now U.S. Pat. No. 7,938,819, which claims the benefit of U.S. Provisional Application No. 60/716,287, filed Sep. 12, 2005, under 35 U.S.C. § 119(e). In addition, this application also claims the benefit of U.S. Provisional Application No. 60/717,726, filed Sep. 15, 2005, under 35 U.S.C. § 119(e). In addition, this application also claims the benefit of U.S. Provisional Application No. 60/727,819, filed Oct. 18, 2005, under 35 U.S.C. § 119(e). The entire disclosures of each of the above-referenced applications are incorporated by reference herein.

FIELD OF THE INVENTION

The inventions described herein relate to devices and associated methods for the treatment of chronic total occlusions. More particularly, the inventions described herein relate to devices and methods for crossing chronic total occlusions and subsequently performing balloon angioplasty, stenting, atherectomy, or other endovascular methods for opening occluded blood vessels.

BACKGROUND OF THE INVENTION

Due to age, high cholesterol and other contributing factors, a large percentage of the population has arterial atherosclerosis that totally occludes portions of the patient's vasculature and presents significant risks to patient health. For example, in the case of a total occlusion of a coronary artery, the result may be painful angina, loss of cardiac tissue or patient death. In another example, complete occlusion of the femoral and/or popliteal arteries in the leg may result in limb threatening ischemia and limb amputation.

Commonly known endovascular devices and techniques are either inefficient (time consuming procedure), have a high risk of perforating a vessel (poor safety) or fail to cross the occlusion (poor efficacy). Physicians currently have difficulty visualizing the native vessel lumen, cannot accurately direct endovascular devices toward visualized lumen, or fail to advance devices through the lesion. Bypass surgery is often the preferred treatment for patients with chronic total occlusions, but less invasive techniques would be preferred.

SUMMARY OF THE INVENTION

To address this and other unmet needs, the present invention provides, in exemplary non-limiting embodiments, devices and methods for the treatment of chronic total occlusions. The disclosed methods and devices are particularly beneficial in crossing coronary total occlusions but may also be useful in other vessels including peripheral arteries and veins. In exemplary embodiments, total occlusions are crossed using methods and devices intended to provide a physician the ability to place a device within the subintimal space, delaminate the connective tissues between layers within the lesion or vessel wall, or remove tissues from the chronic total occlusion or surrounding vessel.

In an aspect of the disclosure, a subintimal device may be used to guide conventional devices (for example guide wires, stents, lasers, ultrasonic energy, mechanical dissection, or atherectomy) within the vessel lumen. Additionally, a subintimal device may be used to delaminate vessel wall layers and also may be used to remove tissue from the occlusive lesion or surrounding vessel wall. In one example, the positioning of a subintimal device or the establishment of a delamination plane between intima and medial layers is achieved through the use of a mechanical device that has the ability to infuse a fluid (for example saline). Fluid infusion may serve to apply a hydraulic pressure to the tissues and aid in layer delamination and may also serve to protect the vessel wall from the tip of the subintimal device and reduce the chance of vessel perforation. The infusion of fluid may be controlled by pressure or by volume.

Subintimal device placement may be achieved with a subintimal device directing catheter. The catheter may orient a subintimal device so that it passes along the natural delamination plane between intima and media. The catheter may orient the subintimal device in various geometries with respect to the vessel. For example, the subintimal device may be directed substantially parallel with respect to the vessel lumen or in a helical pattern such that the subintimal device encircles the vessel lumen in a coaxial fashion. The subintimal device directing catheter may be an inflatable balloon catheter having proximal and distal ends with two wire lumens. One lumen may accept a conventional guide wire while the second lumen may accept the subintimal device. In an alternative embodiment, the wire directing catheter may be a guide catheter with distal geometry that steers the subintimal device with the appropriate orientation to enter the subintimal space.

In an additional disclosure, a subintimal device intended to mechanically delaminate tissue layers may use a device that is inserted into the subintimal space in a first collapsed configuration and is released or actuated into a second expanded configuration. The device may then be withdrawn or manipulated to propagate the area of delamination.

An additional aspect of the disclosure may allow the physician to remove tissues from the lesion or vessel wall. In one embodiment, a subintimal device is circumferentially collapsed around the total occlusion. Tissue removal is performed through simple device withdrawal or through a procedure that first cuts connective tissues (i.e. the intimal layer proximal and distal of the lesion) and then removes the targeted tissue. In another embodiment, a tissue removal device is passed through the lesion within the native vessel lumen. The targeted tissues may be mechanically engaged and removed through device withdrawal.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles. In the drawings.

FIGS. 6A and B are partial sectional views of a expandable delamination catheter;

FIGS. 11A and 11B are schematic illustrations of an alternative subintimal device with a re-entry port;

DETAILED DESCRIPTION OF EXEMPLARY EMBODIMENTS

The following detailed description should be read with reference to the drawings in which similar elements in different drawings are numbered the same. The drawings, which are not necessarily to scale, depict illustrative embodiments and are not intended to limit the scope of the invention.

Figure 1:
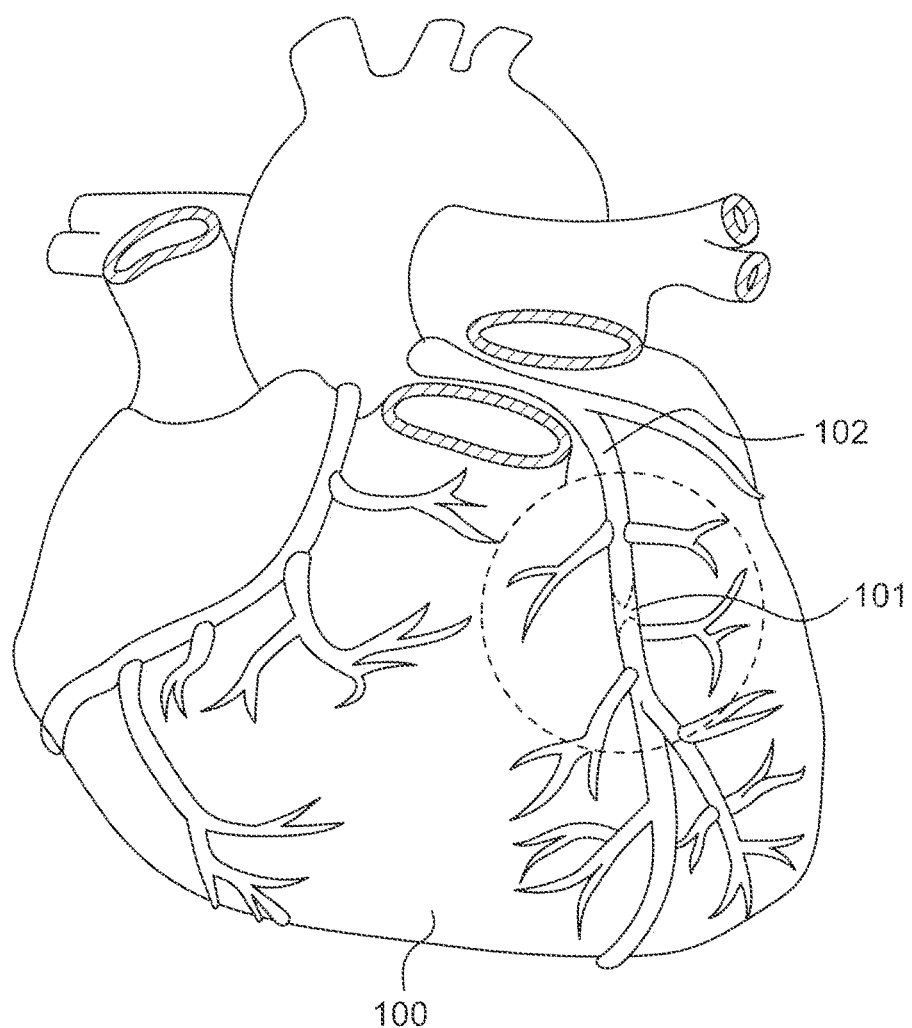
FIG. 1 shows an illustration of a heart showing a coronary artery that contains a chronic total occlusion.
Figure 2:
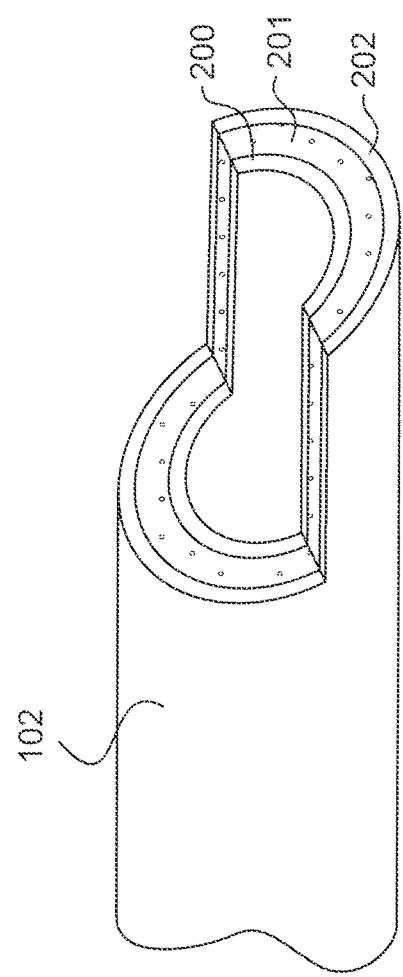
FIG. 2 is a schematic representation of a coronary artery showing the intimal, medial and adventitial layers.

Referring to FIG. 1, a diseased heart 100 includes a chronic total occlusion 101 of a coronary artery 102. FIG. 2 shows coronary artery 102 with intimal layer 200 (for sake of clarity, the multi layer intima is shown as a single homogenous layer). Concentrically outward of the intima is the medial layer 201 (which also is comprised of more than one layer but is shown as a single layer). The transition between the external most portion of the intima and the internal most portion of the media is referred to as the subintimal space. The outermost layer of the artery is the adventitia 202.

Figure 3:
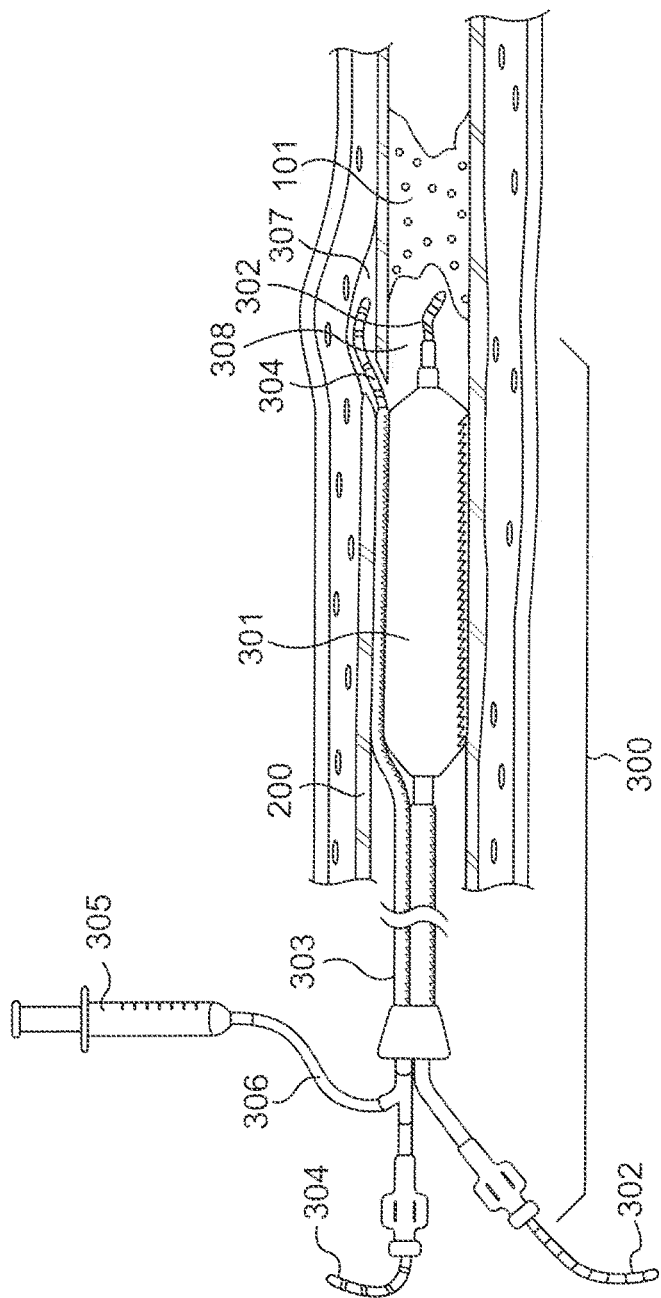
FIG. 3 is a partial sectional view of a subintimal device directing balloon catheter embodiment with fluid infusion through the subintimal device lumen within the device directing catheter.
Figure 4:
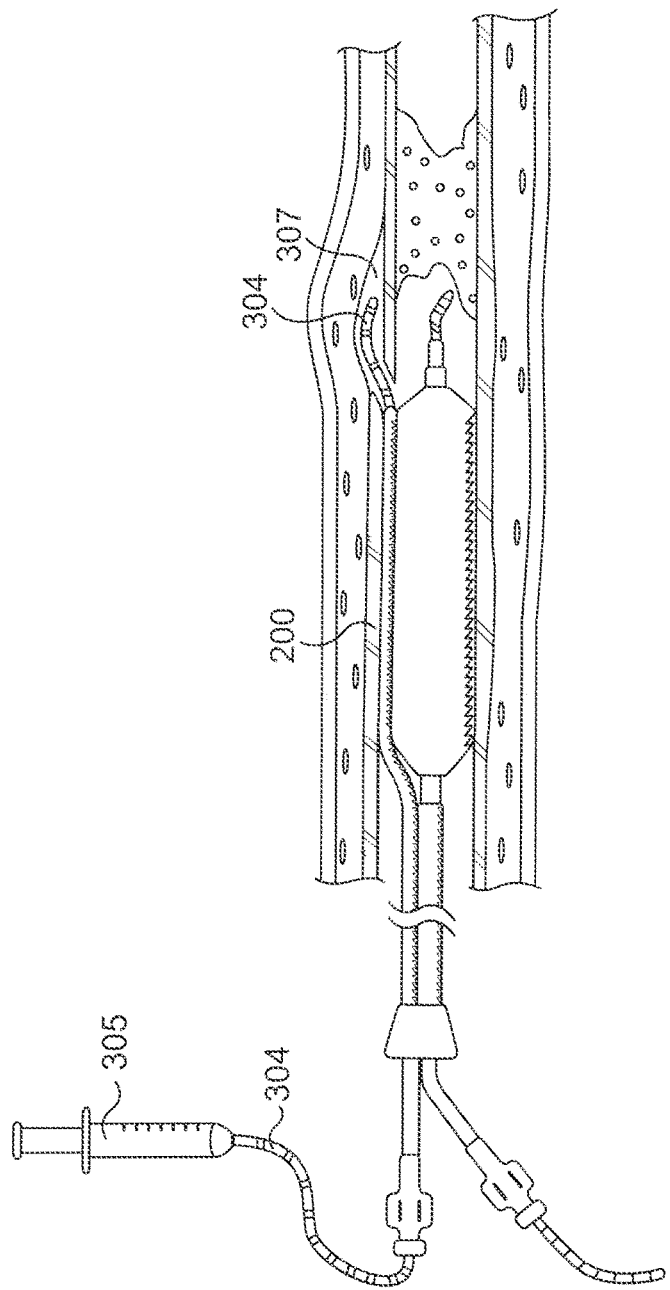
FIG. 4 is a partial sectional view of a subintimal device directing balloon catheter embodiment with fluid infusion through the subintimal device.
Figure 5:
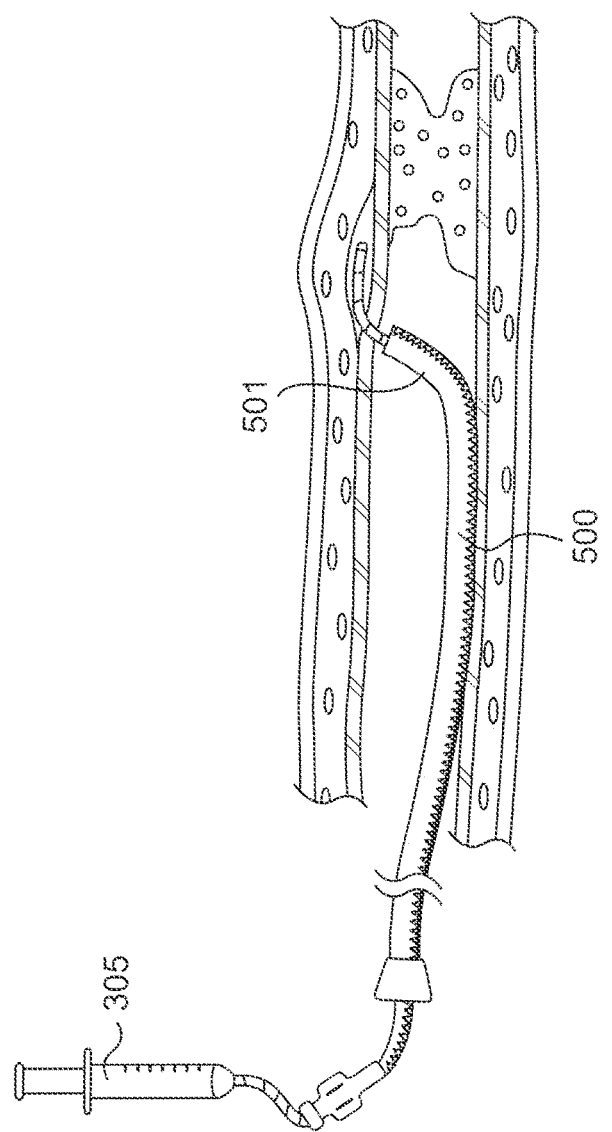
FIG. 5 is a partial sectional view of an additional subintimal device directing guiding catheter embodiment with fluid infusion through the subintimal device.

In an aspect of the disclosure, a subintimal device may be used to guide conventional devices (for example guide wires, stents, lasers, ultrasonic energy, mechanical dissection, or atherectomy) within the vessel lumen. Additionally, a subintimal device may be used to delaminate vessel wall layers and also may be used to remove tissue from the occlusive lesion or surrounding vessel wall. In one embodiment, FIG. 3 shows a subintimal device directing catheter is 300 with its distal balloon 301 that has been advanced over a conventional guide wire 302 and inflated proximal to chronic total occlusion 101. For the sake of clarity, FIG. 4 shows a subintimal device path that is substantially parallel to the vessel lumen, but other orientations (i.e. helical) may also be considered. Subintimal device lumen 303 is positioned adjacent to the intimal layer 200 and subintimal device 304 has been advanced as to perforate the subintimal layer. A fluid source (i.e. syringe) 305 is in fluid communication with subintimal device lumen 303 through infusion lumen 306. Fluid may flow from the fluid source 305 through the subintimal device lumen 303 under a controlled pressure or a controlled volume. The infused fluid may enter the subintimal space 307 directly from the subintimal device lumen 303 or from the volume 308 defined by the distal end of the balloon 301 and the proximal edge of the lesion 101. FIG. 4 shows an alternative fluid infusion path where fluid source 305 is in fluid communication with a lumen within the subintimal device 304. FIG. 5 shows an alternative subintimal device directing guide catheter 500 where the distal end 501 has a predefined shape or the distal end has an actuating element that allows manipulation by the physician intraoperatively.

Another aspect of the disclosure may place a subintimal device within the subintimal space in a first collapsed configuration and releases or actuated the subintimal device to a second expanded configuration. The device may then be withdrawn or manipulated to propagate the subintimal dissection. In one embodiment, FIG. 6A shows a subintimal device with internal expandable element 600 that contains one or more expanding elements contained in exterior sheath 602. FIG. 6B shows exterior sheath in a retracted position allowing expanding elements 601 to elastically expand. The subintimal device is intended to be delivered through the aforementioned subintimal device delivery catheters.

Figure 7A:
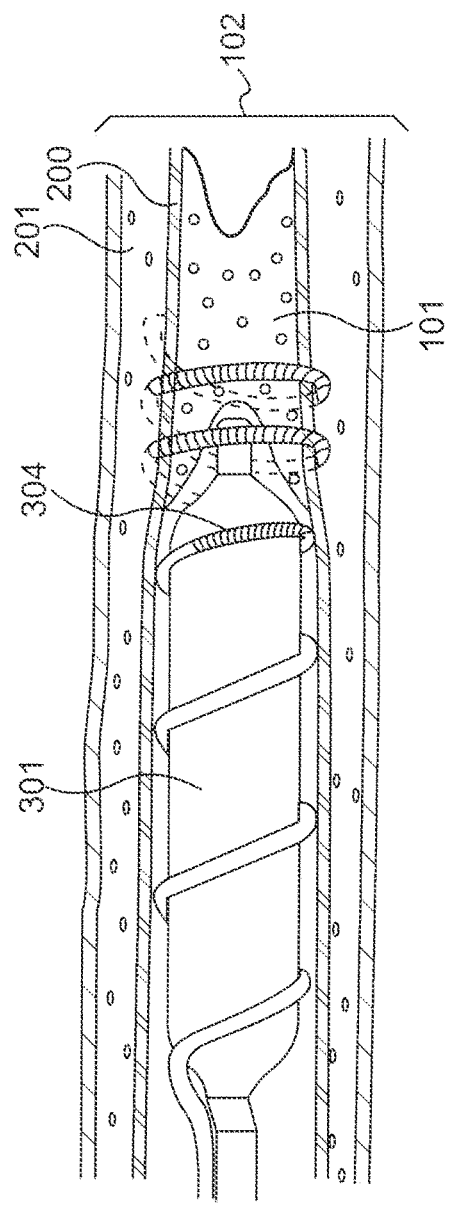
FIGS. 7 A-D are partial sectional views of a circumferential subintimal tissue removal device.
Figure 7B:
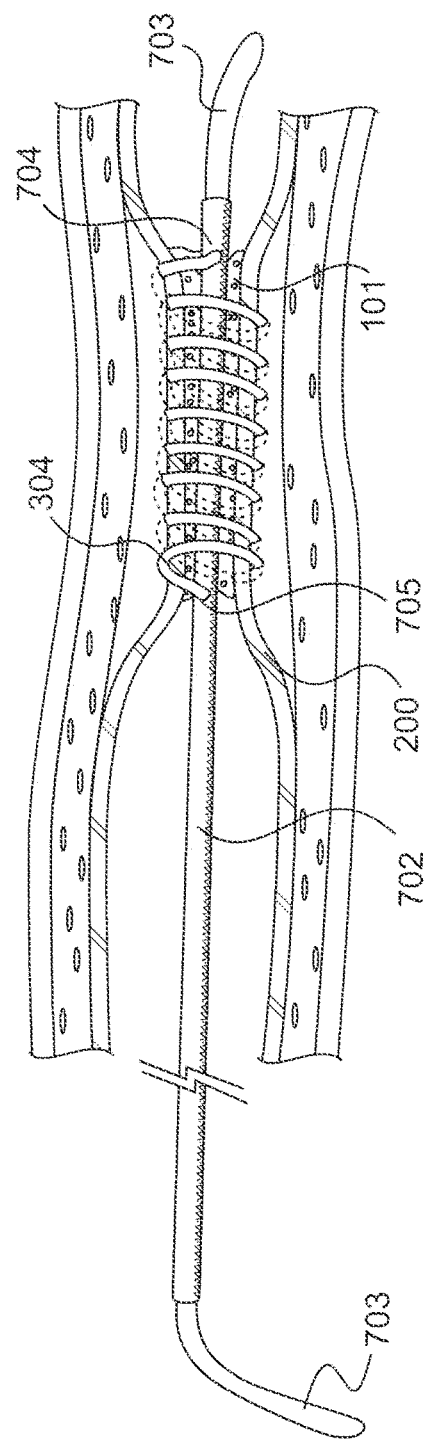
Figure 7C:
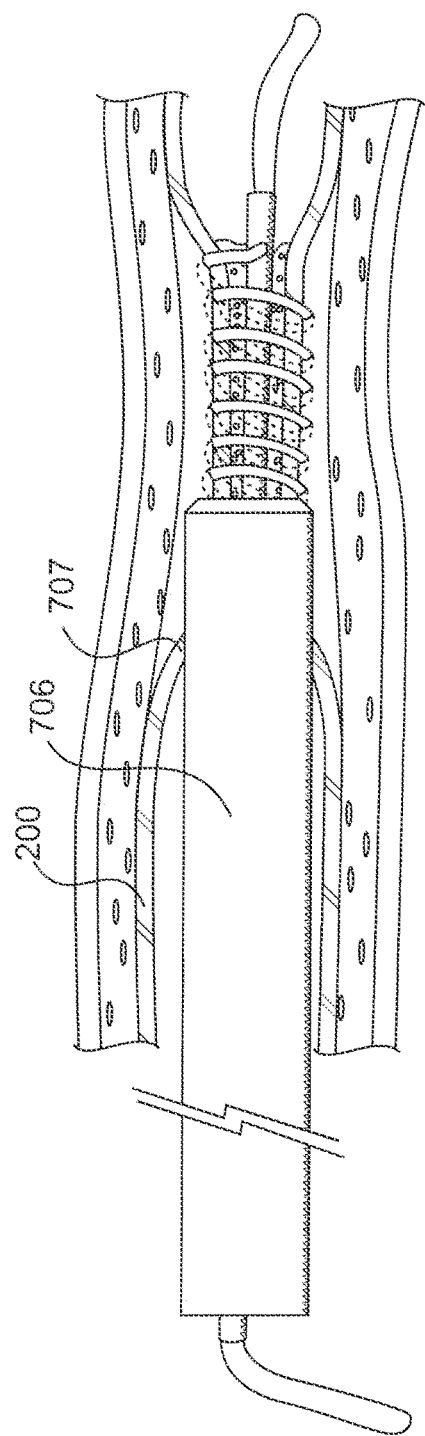
Figure 7D:
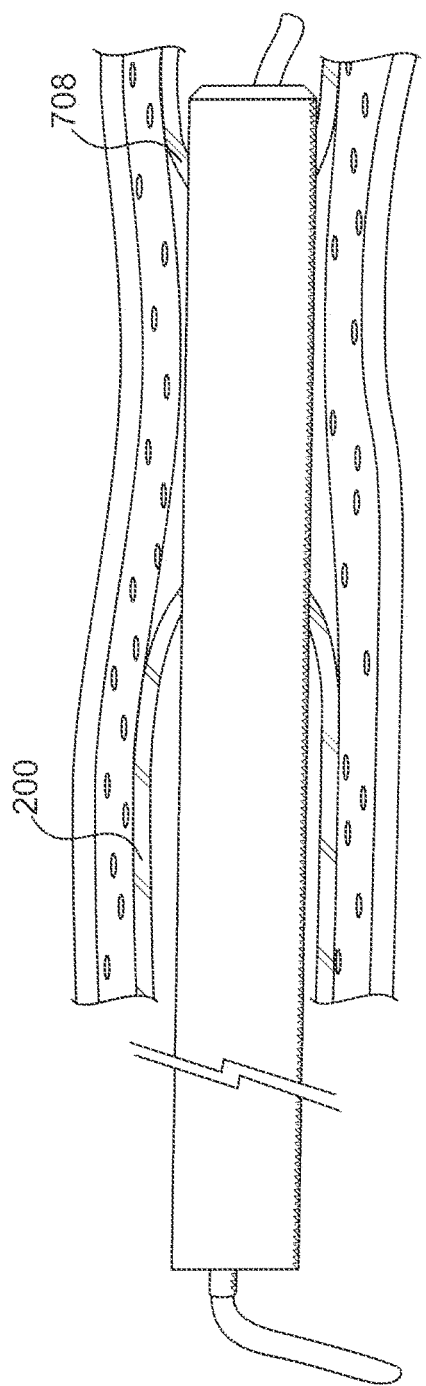

An additional aspect of the disclosure may allow the physician to remove tissues from the lesion or vessel wall. FIG. 7A shows an embodiment where subintimal device directing balloon catheter is inflated within coronary artery 102 just proximal to chronic total occlusion 101. Subintimal device 304 is partially delivered around chronic total occlusion 102 coaxially outside the intimal layer 200 and coaxially inside medial layer 201 in a helical pattern. FIG. 7B shows a subintimal device capture catheter 702 positioned across the chronic total occlusion 101 over conventional guide wire 703 and within subintimal device 304. The distal 704 and proximal 705 ends of the subintimal device have been captured and rotated as to reduce the subintimal device outside diameter and contain the lesion 101 and intima 200 within the coils internal diameter. The device may be withdrawn through the use of a cutting element. For example, FIGS. C and D show the advancement of a cutting element 706 in two stages of advancement showing the cutting of intima 200 proximal of the occlusion 707 and intimal distal of the occlusion 708.

Figure 8A:
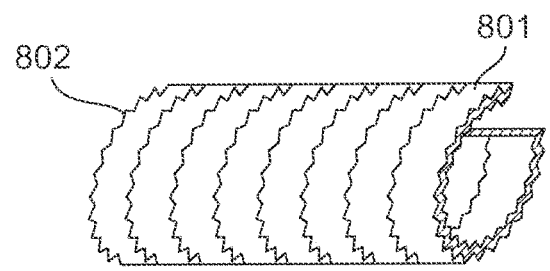
FIGS. 8A-C are an example of subintimal device construction.
Figure 8B:
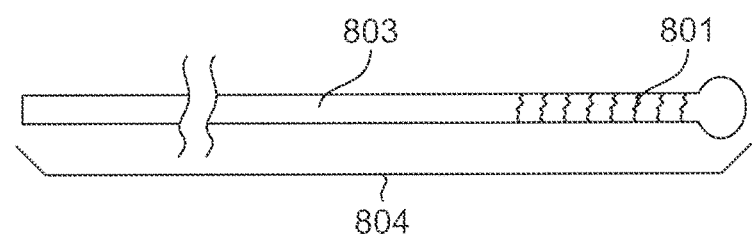
Figure 8C:
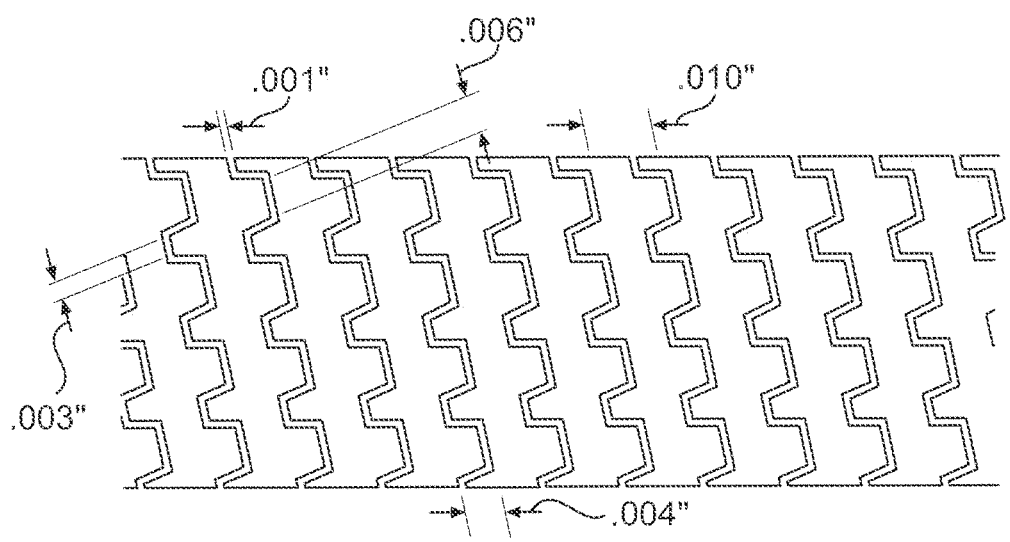

An additional aspect of the subintimal device is the construction of the device body. The flexibility and torquability of the device body can affect the physician's ability to achieve a subintimal path. The subintimal device body may be constructed in part or in to total of a single layer coil with geometric features along the coil length that allow adjacent coils to engage (for example mechanical engagement similar to the teeth of a gear). FIG. 8A shows coil 801 closely wound such that the multitude of teeth 802 along the coil edges are in contact such that the peaks of one coil falls within the valleys of the adjacent coil. A conventional coil reacts to an applied torsional load by diametrically expanding or contracting, thus forcing the wire surfaces within a turn of the coil to translate with respect to its neighboring turn. The construction of coil 801 resists the translation of wire surfaces within the coil thus resisting the diametric expansion or contraction (coil deformation). An increased resistance to coil deformation increases the torsional resistance of the device body while the coiled construction provides axial flexibility. An exemplary construction may include a metallic tube where the coil pattern 801 and teeth 802 are cut from the tube diameter using a laser beam. FIG. 8B shows subintimal device body 804 that is for example a continuous metallic tube with distal laser cut coil segment 801 and proximal solid tube 803. Tube materials include but are not limited to stainless steel and nickel titanium. Alternatively, the coil may be wound from a continuous wire. The wire has a cross section that for example has been mechanically deformed (stamped) to form the teeth and allow coil engagement. FIG. 8C shows an example of a laser cut tooth pattern from the circumference of a tube that has been shown in a flat configuration for purposes of illustration.

Figure 9A:
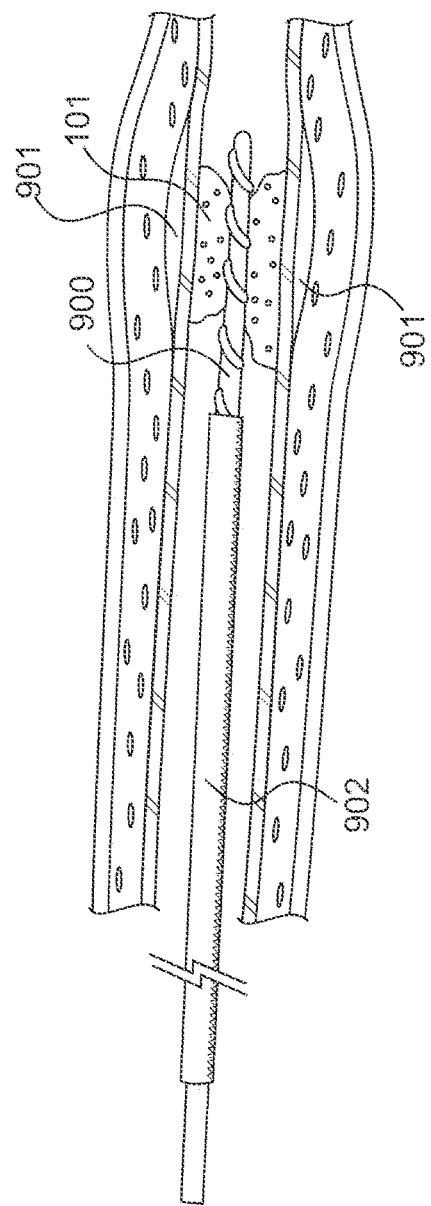
FIGS. 9A and B are partial sectional views of an intraluminal rotational engagement tissue removal device.
Figure 9B:
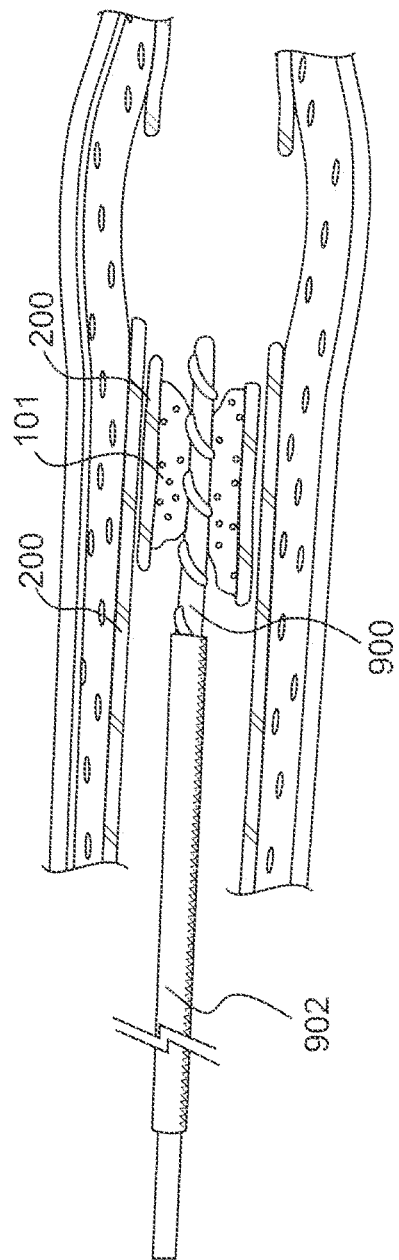

In another embodiment, a tissue removal device may be passed through the lesion within the native vessel lumen. FIG. 9A shows corkscrew device 900 with exterior sheath 902 engaging occlusion after delamination of the intimal layer 901 has been performed by the aforementioned methods and devices. FIG. 9B shows removal of the occlusion and a portion of the intimal layer through axial withdrawal of the corkscrew device.

Figure 10:
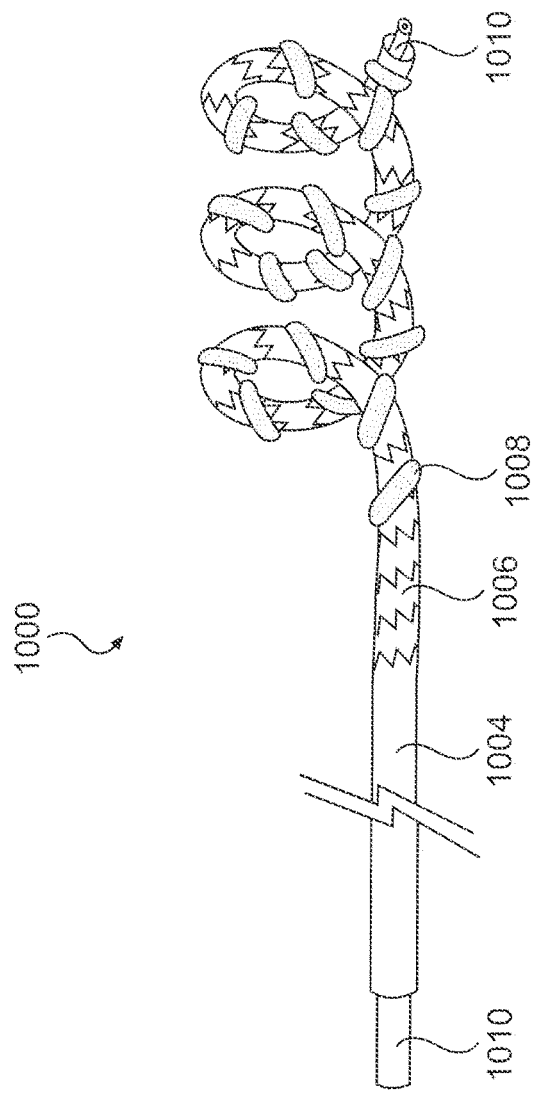
FIG. 10 is a schematic illustration of an alternative subintimal device.

With reference to FIG. 10, an alternative subintimal device 1000 is shown schematically. Subintimal device 1000 is similar to the device shown and described with reference to FIGS. 8A-8C, and may include any of the variants described previously, such as distal atraumatic tip configurations, fluidic dissection mechanisms, etc. Subintimal device 1000 may be sized and shaped for intravascular navigation and includes an elongate tubular shaft 1004, at least a distal portion of which includes a helical interlocking gear 1006 and a helical wire coil 1008 disposed thereon. A helically shaped inner mandrel or tube 1010 may be disposed in the tubular shaft 1004 such that the shaft 1004 rotates freely thereon. The shaft 1004 may have a linear or straight configuration in a relaxed state and a helical configuration (shown) when the helically shaped inner member 1010 is disposed therein. The device 1000 may be disposed in a constraining sheath (not shown) and navigated to the intravascular site, such as the site of an occlusion. When the device 1000 is advanced distally out the end of the constraining sheath or when the sheath is pulled proximally relative thereto, the distal portion of the device 1000 assumes a helical shape as shown. The shaft 1004 may be rotated relative to the inner member 1010 to cause rotation of the helical wire threads 1008, which may be used to engage the vessel wall and advance around an occlusion in a subintimal path as described previously. A bearing (not shown) may be disposed on the inner member 1010 to engage the proximal or distal end of the shaft 1004 to enable the shaft 1004 and the inner member 1010 to be advanced in unison.

With reference to FIGS. 11A and 11B, an alternative subintimal device 1100 is shown schematically. Subintimal device 1100 may be similar to device 1000 described previously, with the helical interlocking gear and helical wire coil eliminated for sake of illustration. Subintimal device 1100 includes an elongate tubular shaft 1102 having a lumen extending therethrough and a re-entry port 1106 disposed distally in the region of the helical shape. In this embodiment, the distal portion of the shaft 1102 may have a helical shape in its relaxed state such that the re-entry port 1106 is always oriented toward the center of the helix as shown in FIG. 11A. With this arrangement, a re-entry device 1110 such as a guide wire or flexible stylet with a tissue penetrating tip may be advanced through the lumen 1104 of the shaft 1102 to exit the re-entry port 1106 as shown in FIG. 11B. This arrangement may be used to establish re-entry of the native lumen of a vessel once the device 1100 traverses an occlusion in the subintimal space.

Figure 12A:
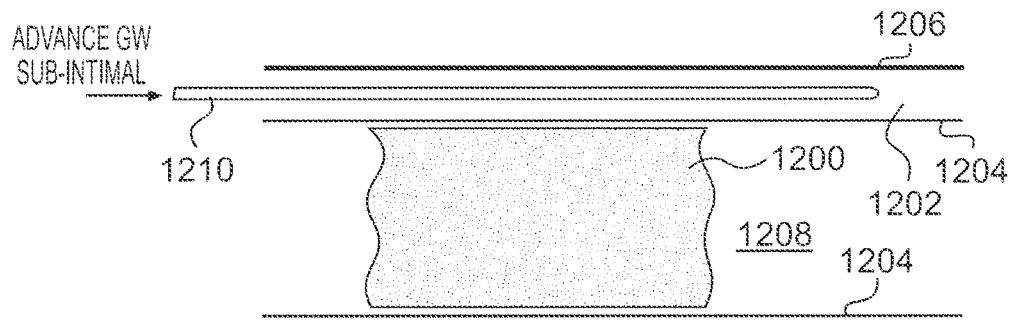
FIGS. 12A-12D are schematic illustrations of a re-entry method using a balloon catheter.
Figure 12B:
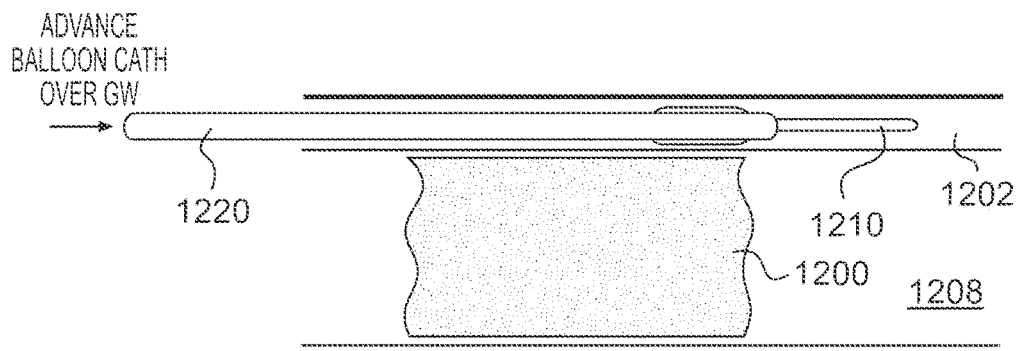
Figure 12C:
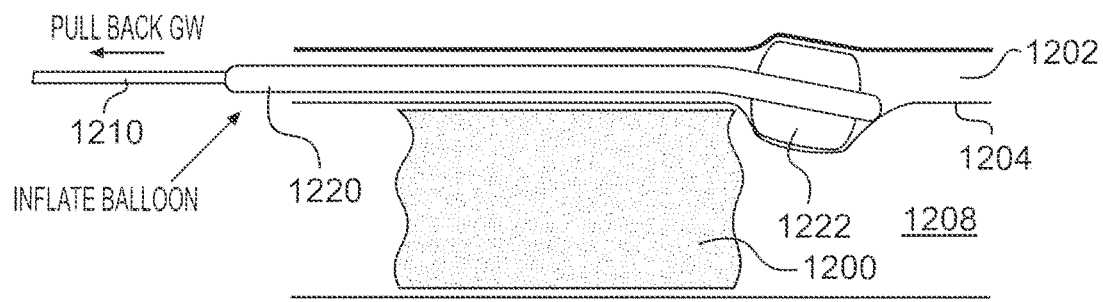
Figure 12D:
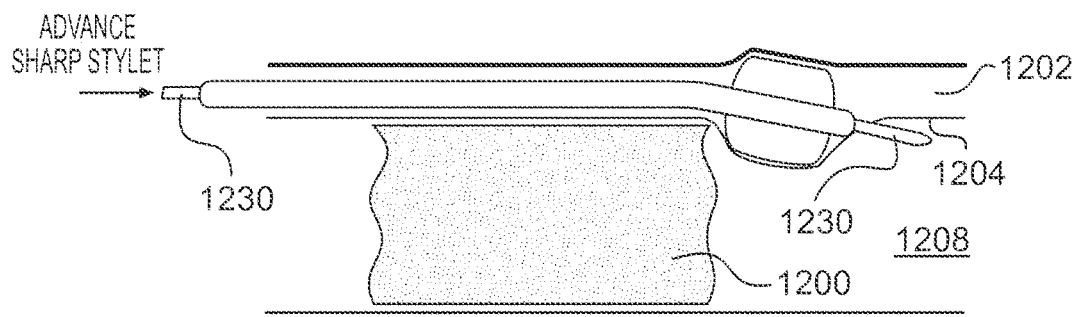

With reference to FIGS. 12A-12D, an alternative re-entry method is schematically shown. In this method, a subintimal device such as guide wire 1210 is advanced into the subintimal space 1202 across an occlusion 1200 in a manner similar to the methods described previously, for example. As shown in FIG. 12A, the guide wire 1210 extends across an occlusion 1200 disposed in subintimal space 1202 between intimal/medial layers 1204 and adventitial layer 1206, where re-entry of the native lumen 1208 distal of the occlusion 1200 is desired. A balloon catheter 1220 is then advanced over the guide wire 1210 until the balloon portion is disposed adjacent the distal end of the occlusion as shown in FIGS. 12B and 12C. The guide wire 1210 is pulled proximally and balloon is then inflated causing radial displacement of the distal end of the balloon catheter 1220 as shown in FIG. 12C. Inflating the balloon of the balloon catheter 1220 orients the tip of the catheter toward the intimal/medial layers 1204. The guide wire 1210 may be removed from the balloon catheter 1220 and a sharpened stylet 1230 or the like may be advanced through the guide wire lumen of the catheter 1220 until the distal end of the stylet 1230 penetrates the intimal/medial layers 1204 as shown in FIG. 12D, thus establishing re-entry from the subintimal path 1202 and into the native lumen 1208.

Figure 13A:
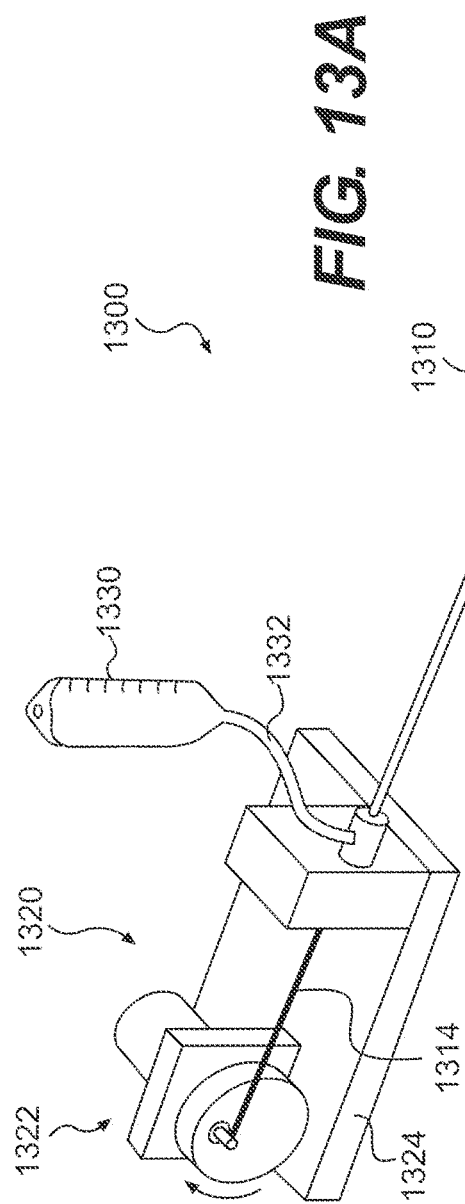
FIGS. 13A and 13B are schematic illustrations of an alternative subintimal device and associated pumping system.
Figure 13B:
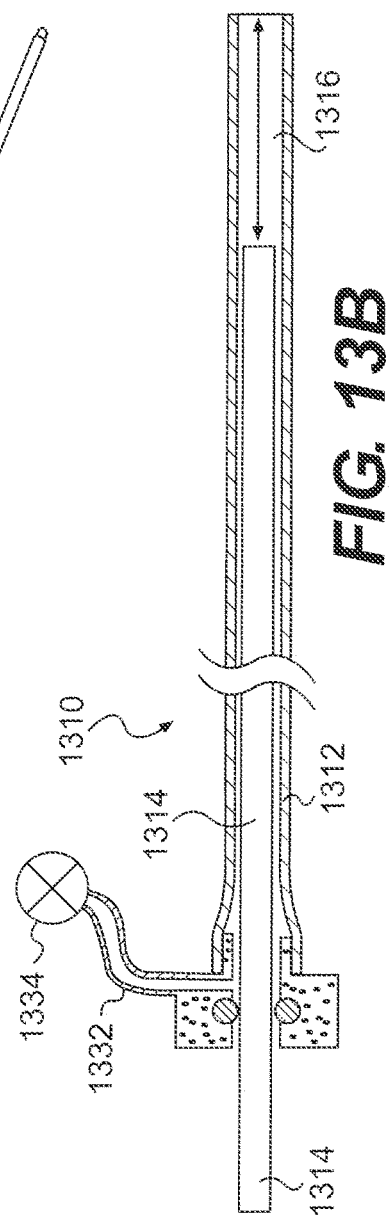

With reference to FIGS. 13A and 13B, an alternative fluidic subintimal system 1300 with subintimal device 1310 and associated pumping system 1320 is shown schematically. The fluidic system 1300 is similar in certain aspects to the arrangements described with reference to FIGS. 3, 4 and 5, the various aspects of which may be combined or used in the alternative as will be appreciated by those skilled in the art. System 1300 includes a subintimal device 1310 which may comprise any of the tubular subintimal devices described herein. Generally, subintimal device 1310 includes a tubular shaft 1312 having a proximal end connected to a pumping mechanism 1320. A plunger rod 1314 is slidingly disposed in the tubular shaft 1312 as shown in FIG. 13B and its proximal end is connected to a linear actuator 1322 of the pumping mechanism as shown in FIG. 13A. As seen in FIG. 13B, a ring seal 1315 is disposed in the lumen of shaft 1312 around the rod 1314. The rod 1314 extends through the tubular shaft 1312 to a point proximal of the distal end thereof to define a pumping chamber 1316. A source of liquid 1330 (e.g., saline bag) is connected to the proximal end of the subintimal device 1310 via a fluid line 1332 and optional valve 1334 to supply liquid to the annular lumen between the rod 1314 and the inner wall of the tubular shaft 1312. As the linear actuator moves the rod 1314 back and forth in the tubular shaft 1312, liquid is caused to be expelled out of the chamber 1316 in a pulsatile fashion, which may be used to hydraulically dissect tissues to define a subintimal path as described previously, for example. The stroke length, stroke rate and stroke volume may be adjusted to achieve the desired effect. For example, the stroke volume of the chamber 1316 may be relatively small (0.01 cc-1.0 cc, for example) such that liquid exits the chamber 1316 with high energy that dissipates quickly to minimize trauma to tissues as they are dissected.

From the foregoing, it will be apparent to those skilled in the art that the present invention provides, in exemplary non-limiting embodiments, devices and methods for the treatment of chronic total occlusions. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of facilitating treatment of a blood vessel, comprising:

advancing a guidewire within a vascular wall of the blood vessel past an occlusion disposed within a lumen of the blood vessel;

advancing a balloon catheter over the guidewire until a balloon disposed on a distal portion of the balloon catheter is disposed adjacent a distal end of the occlusion;

withdrawing the guidewire from the balloon catheter; and inflating the balloon within the vascular wall to orient a distal end of the balloon catheter towards the lumen of the blood vessel.

2. The method of claim 1, wherein the balloon catheter includes a lumen extending distally to a distal opening proximate the distal end of the balloon catheter.

3. The method of claim 2, wherein inflating the balloon within the vascular wall orients the distal opening towards the lumen of the blood vessel.

4. The method of claim 1, wherein at least a portion of an exterior surface of the balloon catheter is exposed between a proximal end of the balloon and a distal end of the balloon.

5. The method of claim 1, further comprising:
advancing a sharpened stylet through the balloon catheter until a distal end of the sharpened stylet penetrates the vascular wall and is positioned within the lumen of the blood vessel.

6. The method of claim 5, wherein the distal end of the balloon catheter directs the distal end of the sharpened stylet toward the lumen of the blood vessel.

7. The method of claim 1, wherein a portion of an exterior surface of the balloon catheter is exposed between a proximal end of the balloon and a distal end of the balloon;
wherein the portion of the exterior surface is defined by a longitudinal dimension that is greater than a circumferential dimension.

8. The method of claim 1, wherein at least a portion of the balloon is inflated in a direction away from the lumen of the blood vessel.

9. A method of facilitating treatment of a blood vessel, comprising:
advancing a guidewire within a subintimal space of the blood vessel until a distal end of the guidewire is positioned distal of a total occlusion disposed within a lumen of the blood vessel;

advancing an intravascular device over the guidewire until a balloon disposed on a distal portion of an elongate shaft of the intravascular device is disposed adjacent a distal end of the occlusion, wherein the guidewire is slidably disposed within a lumen of the elongate shaft;

withdrawing the guidewire from the lumen of the elongate shaft; and inflating the balloon within the subintimal space to orient a distal opening of the elongate shaft towards the lumen of the blood vessel.

10. The method of claim 9, wherein the lumen of the elongate shaft extends within the elongate shaft to the distal opening.

11. The method of claim 10, wherein the distal opening is disposed at a distalmost end of the elongate shaft.

12. The method of claim 9, wherein a radially outwardly facing surface of the elongate shaft is exposed between a proximal end of the balloon and a distal end of the balloon.

13. The method of claim 9, further comprising:
advancing a sharpened stylet through the lumen of the elongate shaft until a distal end of the sharpened stylet penetrates through a wall of the blood vessel and into the lumen of the blood vessel.

14. The method of claim 13, wherein the distal end of the elongate shaft directs the distal end of the sharpened stylet toward the lumen of the blood vessel.

15. The method of claim 9, wherein a portion of a radially outwardly facing surface of the elongate shaft is exposed between a proximal end of the balloon and a distal end of the balloon;
wherein the portion of the radially outwardly facing surface is defined by a longitudinal dimension and a circumferential dimension;
wherein the longitudinal dimension is greater than the circumferential dimension.

16. The method of claim 9, wherein at least a portion of the balloon is inflated in a direction away from the lumen of the blood vessel.

17. A method of facilitating treatment of an occlusion within a lumen of a blood vessel, comprising:
advancing a guidewire within a vascular wall of the blood vessel until a distal end of the guidewire is disposed distal of the occlusion;

maintaining the distal end of the guidewire within the vascular wall and distal of the occlusion while advancing an intravascular device over the guidewire until a balloon disposed on a distal portion of an elongate shaft of the intravascular device is disposed distal of the occlusion;

withdrawing the guidewire from the intravascular device;

inflating the balloon within the vascular wall to orient a distal opening of the elongate shaft towards the lumen of the blood vessel; and advancing a distal end of a sharpened stylet out of the distal opening, through at least one layer of the vascular wall, and into the lumen of the blood vessel distal of the occlusion.

18. The method of claim 17, wherein:
prior to inflating the balloon, the distal portion of the elongate shaft is oriented substantially parallel to the lumen of the blood vessel; and
after inflating the balloon, the distal portion of the elongate shaft is oriented at an oblique angle to the lumen of the blood vessel.

19. The method of claim 17, wherein the balloon includes:
a proximal end and a distal end;
a first balloon portion extending from the proximal end to the distal end, the first balloon portion being configured to extend radially outward in a first direction from the elongate member; and
a second balloon portion extending from the proximal end to the distal end, the second balloon portion being configured to extend radially outward in a second direction from the elongate member;
wherein the second direction is substantially opposite the first direction.

20. The method of claim 19, wherein a radially outwardly facing surface of the elongate shaft is exposed between the first balloon portion and the second balloon portion.

* * * * *